(12) United States Patent
Findeisen et al.

(10) Patent No.: US 8,435,757 B2
(45) Date of Patent: May 7, 2013

(54) MASS SPECTROMETRIC ENDOPEPTIDASE ASSAY

(75) Inventors: Peter Findeisen, Schriesheim (DE); Michael Neumaier, Edingen-Neckarshause (DE)

(73) Assignee: Bruker Daltonik, GmbH, Bremen (DE)

( * ) Notice: Subject to any disclaimer, the term of this patent is extended or adjusted under 35 U.S.C. 154(b) by 226 days.

(21) Appl. No.: 12/785,909

(22) Filed: May 24, 2010

(65) Prior Publication Data

US 2010/0317044 A1    Dec. 16, 2010

(30) Foreign Application Priority Data

Jun. 12, 2009   (DE) .................. 10 2009 024 720

(51) Int. Cl.
*C12Q 1/37*    (2006.01)
(52) U.S. Cl.
USPC .......................................................... 435/24
(58) Field of Classification Search ............ 435/24
See application file for complete search history.

(56) References Cited

U.S. PATENT DOCUMENTS

| 6,458,533 | B1 * | 10/2002 | Felder et al. ................. | 435/6.16 |
| 7,067,248 | B2 | 6/2006 | Hruby et al. | |
| 2008/0070804 | A1 * | 3/2008 | Zweig .............................. | 506/26 |
| 2008/0206787 | A1 | 8/2008 | Wu et al. | |
| 2009/0305327 | A1 | 12/2009 | Franzen et al. | |
| 2010/0028916 | A1 | 2/2010 | Ambar et al. | |

FOREIGN PATENT DOCUMENTS

| EP | 1 808 493 A2 | | 7/2007 |
| WO | WO 03/075833 | * | 9/2003 |
| WO | WO 2007/098859 | * | 9/2007 |

OTHER PUBLICATIONS

Kozlov I. et al. A High Complexity Multiplexed Solution Phase Assay for Profiling Protease Activity on Micorarrays. Combinatorial Chemistry & High Throughput Screening 11(1)24-35, 2008.*
Peccerella T. et al. Endoprotease Profiling with Double Tagged Peptide Substrates. Clinical Chemistry 56(2)272-280, 2010.*
Findeisen P. et al. Spiking of Serum Specimens with Exogenous Reporter Peptides for MS Based Protease Profiling as Diagnostic Tool. Rapid Communications Mass Spectrometry 22(8)1223-1229, Apr. 30, 2008.*
Basak, et al., "Radiolabeled Biotinyl Peptides as Useful Reagents for thhe Study of Proteolytic Enzymes", Analytical Biochemistry 209, pp. 306-314, 1993, Academic Press, Inc.
Kozlov, et al., "A High-Complexity, Multiplexed Solution-Phase Assay for Profiling Protease Activity on Microarrays", Combinatorial Chemistry & High Throughput Screening, 2008, vol. 11, No. 1, pp. 24-35, Bentham Science Publishers, Ltd.
Peccerella, et al., "Endoprotease Profiling with Double-Tagged Peptide Substrates: A New Diagnostic Approach in Oncology", Clinical Chemistry 56-2, 2010, pp. 272-280.
Villanueva, et al., "Differential Exoprotease Activites Confer Tumor-Specific Serum Peptidome Patterns", the Journal of Clinical Investigation, vol. 116, No. 1, Jan. 2006, pp. 271-284.

* cited by examiner

*Primary Examiner* — Ralph Gitomer
(74) *Attorney, Agent, or Firm* — Robic, LLP

(57) ABSTRACT

The activity of a selected endopeptidase in a body fluid is determined by the mass spectrometric measurement of the reaction products of reporter substrate molecules added to the body fluid. Each reporter substrate molecule includes a peptide with the cleavage motif of the endopeptidase, an anchor group A1 on one side of the cleavage site and a different anchor group A2 on the other side of the cleavage site. One anchor is used to extract the reporter substrate molecules from the body fluid and the other anchor is used to extract digest fragments of the reporter molecules from the body fluid. Mass markers allow several reporter substrates to be used simultaneously in the same body fluid sample to measure the activity of different types of endopeptidase.

9 Claims, 2 Drawing Sheets

SEQUENCE LISTING

<160> NUMBER OF SEQ ID NOS: 8

<210> SEQ ID NO 1
<211> LENGTH: 18
<212> TYPE: PRT
<213> ORGANISM: Artificial Sequence
<220> FEATURE:
<223> OTHER INFORMATION: biotinylated peptide substrate for cathepsin D
      endopeptidase
<220> FEATURE:
<221> NAME/KEY: A01
<222> LOCATION: (1)..(1)
<223> OTHER INFORMATION: 2-Aminobutyric acid
<220> FEATURE:
<221> NAME/KEY: A02
<222> LOCATION: (2)..(2)
<223> OTHER INFORMATION: 6-Aminocaproic acid
<220> FEATURE:
<221> NAME/KEY: A11
<222> LOCATION: (11)..(11)
<223> OTHER INFORMATION: 6-Aminocaproic acid
<220> FEATURE:
<221> NAME/KEY: A18
<222> LOCATION: (18)..(18)
<223> OTHER INFORMATION: dextrorotatory amino acid alanine

<400> SEQUENCE: 1

Xaa Xaa Glu Arg Gly Phe Phe Tyr Thr Pro Xaa His His His His His
1               5                   10                  15

His Xaa

<210> SEQ ID NO 2
<211> LENGTH: 8
<212> TYPE: PRT
<213> ORGANISM: Artificial Sequence
<220> FEATURE:
<223> OTHER INFORMATION: fragment of peptide substrate for cathepsin D
      endopeptidase
<220> FEATURE:
<221> NAME/KEY: A01
<222> LOCATION: (1)..(1)
<223> OTHER INFORMATION: 6-Aminocaproic acid
<220> FEATURE:
<221> NAME/KEY: A08
<222> LOCATION: (8)..(8)
<223> OTHER INFORMATION: dextrorotatory amino acid alanine

<400> SEQUENCE: 2

Xaa His His His His His His Xaa
1               5

<210> SEQ ID NO 3
<211> LENGTH: 10
<212> TYPE: PRT
<213> ORGANISM: Artificial Sequence
<220> FEATURE:
<223> OTHER INFORMATION: fragment of peptide substrate for cathepsin D
      endopeptidase
<220> FEATURE:
<221> NAME/KEY: A03
<222> LOCATION: (3)..(3)
<223> OTHER INFORMATION: 6-Aminocaproic acid
<220> FEATURE:
<221> NAME/KEY: A10
<222> LOCATION: (10)..(10)
<223> OTHER INFORMATION: dextrorotatory amino acid alanine

<400> SEQUENCE: 3

Thr Pro Xaa His His His His His His Xaa
1               5                   10

```
<210> SEQ ID NO 4
<211> LENGTH: 8
<212> TYPE: PRT
<213> ORGANISM: Artificial Sequence
<220> FEATURE:
<223> OTHER INFORMATION: peptide substrate for cathepsin D endopeptidase

<400> SEQUENCE: 4

Glu Arg Gly Phe Phe Tyr Thr Pro
1               5

<210> SEQ ID NO 5
<211> LENGTH: 8
<212> TYPE: PRT
<213> ORGANISM: Artificial Sequence
<220> FEATURE:
<223> OTHER INFORMATION: peptide substrate for cancer procoagulant
      cystine protease

<400> SEQUENCE: 5

Trp Lys Pro Tyr Asp Ala Ala Asp
1               5

<210> SEQ ID NO 6
<211> LENGTH: 18
<212> TYPE: PRT
<213> ORGANISM: Artificial Sequence
<220> FEATURE:
<223> OTHER INFORMATION: biotinylated peptide substrate for cancer
      procoagulant cystine protease
<220> FEATURE:
<221> NAME/KEY: A01
<222> LOCATION: (1)..(1)
<223> OTHER INFORMATION: 2-Aminobutyric acid
<220> FEATURE:
<221> NAME/KEY: A02
<222> LOCATION: (2)..(2)
<223> OTHER INFORMATION: 6-Aminocaproic acid
<220> FEATURE:
<221> NAME/KEY: A11
<222> LOCATION: (11)..(11)
<223> OTHER INFORMATION: 6-Aminocaproic acid
<220> FEATURE:
<221> NAME/KEY: A18
<222> LOCATION: (18)..(18)
<223> OTHER INFORMATION: dextrorotatory amino acid threonine

<400> SEQUENCE: 6

Xaa Xaa Trp Lys Pro Tyr Asp Ala Ala Asp Xaa His His His His His
1               5                   10                  15

His Xaa

<210> SEQ ID NO 7
<211> LENGTH: 8
<212> TYPE: PRT
<213> ORGANISM: Artificial Sequence
<220> FEATURE:
<223> OTHER INFORMATION: fragment of peptide substrate for cancer
      procoagulant cystine protease
<220> FEATURE:
<221> NAME/KEY: A01
<222> LOCATION: (1)..(1)
<223> OTHER INFORMATION: 6-Aminocaproic acid
<220> FEATURE:
<221> NAME/KEY: A08
<222> LOCATION: (8)..(8)
<223> OTHER INFORMATION: dextrorotatory amino acid threonine

<400> SEQUENCE: 7

Xaa His His His His His His Xaa
1               5
```

```
<210> SEQ ID NO 8
<211> LENGTH: 4
<212> TYPE: PRT
<213> ORGANISM: Artificial Sequence
<220> FEATURE:
<223> OTHER INFORMATION: fragment of peptide substrate for cancer
      procoagulant cystine protease

<400> SEQUENCE: 8

Asp Ala Ala Asp
1
```

MASS SPECTROMETRIC ENDOPEPTIDASE ASSAY

This application claims benefit to application Germany 10 2009 024 720 3 filed Jun. 12, 2009.

BACKGROUND

The invention relates to the determination of the activity (concentration multiplied by reaction rate) of selected endopeptidases in body fluids by mass spectrometric measurements of the reaction products of added reporter substrates. Mass spectrometric diagnostics by analyses of substance mixtures extracted from body fluids are still in their infancy. This is true for both the development of diagnostic measurement and evaluation methods as well as for the official validation of the mass spectrometers or mass spectrometric procedures for diagnostic purposes. The first mass spectrometric methods which are validated for medical diagnostics are now coming onto the market. In Europe, the validation is based on an IVD Compatibility Declaration (CE) by manufacturers, who are subject to a special quality audit in accordance with DIN EN ISO 13485:2003, for example. IVD is the abbreviation for "in vitro diagnostics". In Germany, this validation process is regulated by the Medical Products Act (MPG), which is based on the European Directive 98/79/EC. Outside Europe, validation directives usually are provided by official bodies.

In the publication "Differential exopeptidase activities confer tumor-specific serum peptidome patterns", J. Villanueva et al., J. Clin. Invest., 116: 271-284 (2006), it was shown that peptides in blood serum which are produced by enzymatic digestion are not just useless garbage, as had largely been assumed, but that it is possible to find characteristic patterns therein to identify disease-specific enzyme activities. The authors were able to use the digest peptide patterns of the endogenous blood proteins which are present in higher concentrations, such as fibrinogen or other clotting factors, to distinguish between three different types of cancer as well as healthy control samples. The endogenous blood peptides including the digestion products of larger proteins were measured after a broadband extraction on magnetic beads with hydrophobic surfaces in a time-of-flight mass spectrometer with ionization by matrix-assisted laser desorption (MALDI), where all extracted peptides from a sample can be recorded simultaneously in a single mass spectrum. The analysis of these peptides showed that digestion reactions of the proteins brought about by the enzymes in the blood serum did not proceed in the same way in all samples but rather that the nature and rate of the reactions was different depending on the disease. Furthermore, it was possible to show that not all proteins in the blood are digested. Practically no digest peptides of the most prevalent proteins, i.e. the albumins and globulins, can be found. These highly molecular proteins are protected by their structure in such a way that they resist attacks by enzymes. The digest peptides could be mostly assigned to the clotting factors such as fibrinogen a or C3f.

Blood consists mainly of water (over 90%), various types of minute blood particles, small quantities of salts, several non-protein organic substances, and around seven percent is made up of proteins, of which albumins and globulins form the largest part. The next prevalent are the so-called clotting factors, above all fibrinogen. The peptidases which are of interest as possible biomarkers here are present in the blood samples at lower concentrations of usually far below $10^{-6}$ percent down to $10^{-10}$ percent, and elude a direct mass spectrometric measurement; they can therefore only be measured indirectly by their effects. One type of such an indirect measurement by an enzymatic effect has been described in the work cited above. Today, in a good mass spectrometer the direct measurement and evaluation of protein profiles from blood serum is generally limited to the concentration range of $10^{-1}$ to $10^{-4}$ percentage by weight.

The activity of the peptidases cannot only be measured in blood, but also quite generally in all body fluids. The term "body fluid" here shall therefore encompass all fluids of the body in the most general sense, i.e. in addition to blood also lymphs, liquor, cell homogenates and cell extracts, for example, and also fluids excreted by the body such as urine, sweat, lacrimal fluid and others, even if these analyses often focus on blood. If the term "blood sample" is used below, it can refer to "whole blood", "blood serum" or also "blood plasma". If the blood particles are removed from blood which has just been taken, the "whole blood", by centrifuging, for example, the "blood plasma" is obtained, which still contains all clotting factors, above all fibrinogen. If it is to be stored or transported, the blood plasma must be prevented from coagulating by adding anticoagulants. If, on the other hand, the whole blood is coagulated, fibrinogen is broken down to fibrins through different stages with the assistance of other clotting factors. These fibrins polymerize and together with the blood corpuscles form the blood clot. If this blood clot is removed by centrifugation or any other means, one obtains the "blood serum", which now contains (almost) no coagulants.

The smaller proteins with molecular weights of up to several thousand atomic mass units, which consist of only a few tens of amino acids, are called peptides; unless otherwise specifically mentioned, they are included here in the term "proteins". The vast majority of peptides in body fluids are so-called "digest peptides" which are created as a result of the continuous enzymatic stronger or weaker digestion of larger proteins. In blood, the digestion concerns fibrinogen, for example, and in cells, endogenous proteins which are no longer needed. Proteins are digested by enzymes which are usually called "peptidases", or also "proteases" or "proteinases" and which exist in hundreds or even thousands of different types in human and animal bodies. The peptidases are classified into endopeptidases and exopeptidases according to their type of effect.

"Endopeptidases" cleave proteins inside the amino acid chain of the proteins, but only if certain enzyme-specific "cleavage motifs" are present in the chain of the amino acids. One example of this is the familiar digest enzyme trypsin which always cleaves adjacent to the amino acids lysine and arginine. The cleavage motif at which a specific peptidase cuts can consist of a single specific amino acid and also of an enzyme-specific chain of several amino acids. Blood generally contains only endopeptidases, which have more complicated motifs of several amino acids and which are specialized in the digestion of certain proteins, because otherwise all blood proteins would be attacked in a life-threatening way.

"Exopeptidases", on the other hand, indiscriminately break down peptides from the end: One amino acid after the other is removed, generally creating a mixture of digest peptides which each differ by one amino acid and thus enabling the sequence of the broken-down protein to be identified in a mass spectrometric measurement by virtue of the mass differences. Exopeptidases, which break down two or even three amino acids as a group, are less common. Depending on the exact type, exopeptidases work either from the C-terminal or from the N-terminal end of the protein (carboxyl exopeptidases and amino exopeptidases). The mixtures of digestion products created by exopeptidases are also called "digestion ladders". The proteins naturally occurring in blood are usually protected by folding patterns which resist the attack of the ever-present exopeptidases on the terminal amino acids.

All enzymes have a catalytic effect on one or more target substances, which are termed the "substrate" of the enzyme, and which are modified by the catalytic activity of the enzyme in a way which is characteristic of the enzyme. The enzymes are therefore not used up by their activity, but rather their activity gradually decreases over quite long periods of some days, the activities of other enzymes or even self-digestion also playing a part. The half lives of the enzymes' activity amount to a few days; freezing prevents the activity from diminishing.

The rate of the catalytic reactions of the enzymes and hence the change to the substrates is very different. "Sluggish enzymes" have a reaction rate of around one substrate molecule per second and enzyme molecule; fast enzymes can exhibit a reaction rate of up to 100,000 substrate molecules per second and enzyme molecule. The fastest known enzyme is catalase, which breaks down hydrogen peroxide which is toxic to the body. Fast reaction rates require that sufficient substrate molecules are available, however, and also that diffusion does not restrict the supply. The peptidases, which digest proteins and peptides, usually have reaction rates of around 100 to 1,000 substrate molecules per second and per molecule if there is sufficient supply.

Before a mass spectrometric measurement, the reaction products of enzymes, for example, must be extracted from the body fluid. One option is to use broadband extractions, which bind almost all peptides from the sample to differently coated, actively binding solid surfaces, for example. Of greater interest here, however, are extraction methods which are selectively designed for different "anchor groups" and essentially only bind those molecules which are equipped with the anchor groups. This can occur via chelate-like bonded metal atoms of various types, via substance-specific ligand bonds, and also by custom-made protein-specific bonds similar to the antigen-antibody bonds, for example.

The indirect measurement of the enzyme activity in blood by measuring the reaction products is a breakthrough for diagnostic applications of biomarkers, but also has its disadvantages which are caused by the variability of the composition of blood. These disadvantages can largely be avoided by directing the enzyme activity towards artificial "reporter substrate molecules" added in a standardized way.

Endopeptidases, which have complicated cleavage motifs with a specific sequence of amino acids, are safely identified by the effect they have on appropriately composed reporter substrate molecules and their activity can be measured indirectly by the reaction products. Depending on the duration and rate of the reactions, the occurrence of the reaction products will be many orders of magnitude higher than the molecules of the endopeptidases themselves. If one molecule of an endopeptidase cleaves 100 molecules of a reporter substrate per second, for example, then one million cleavage product molecules per peptidase molecule are present after only three hours. This reaction rate is not even high, rather below average. The prerequisite, however, is the supply of a sufficiently large quantity of reporter substrate molecules, which must therefore be present in a very high concentration in order not to bring about any diffusion-controlled deceleration of the activity.

So if a certain endopeptidase is present in the blood at a concentration of only $10^{-8}$ percent then, after adding a suitable substrate at a concentration of around one percent, reaction products at a concentration of around one hundredth of a percent are present after only three hours incubation time. Around every hundredth substrate molecule is cleaved. This concentration is ideal for an extraction with subsequent mass spectrometric determination.

The "activity" of an enzyme is given by the product of its concentration and its reaction rate. The reaction rate of the reporter substrate molecules as a result of the endopeptidases is strongly dependent on the temperature, most enzymes operate best at 37° C. (approx. 99° F.), i.e. at human body temperature. A temperature which is around five to ten degrees Celsius (9-18° F.) lower reduces the rate of the reaction by around half each time. A reliable measurement of the activity therefore requires incubation under specified conditions. The pH value also plays a role and has to be controlled correctly.

The quantities of specific reaction products produced by the enzymes can serve as biomarkers to identify illnesses. It is known that different types of cancer secrete different types of endopeptidases to a much greater extent into the blood, said endopeptidases cleaving substrates with very specific cleavage motifs. The precise knowledge of their activity in the blood can be used to detect and identify these types of cancer.

DE 10 2006 009 083 A1 (J. Franzen et al.; corresponding to WO 2007/098859 A1) discloses a method of measuring the peptidase activity which uses the addition of exogenous probe substrates (called "reporter substrate molecules" here), which are each provided with an anchor group for a substance-specific extraction. Using exogenous substances with anchor groups as substrates to measure the peptidase activities eliminates many of the disadvantages which exist when analyzing digestion products of endogenous proteins. There is still the disadvantage that this method has a small dynamic range of measurement, however. In addition to the reaction products to be measured, the reporter substrate molecules which have not been broken down are also always extracted with the anchor group. For slow reactions or for very low peptidase concentrations, both of which supply only a small fraction of the reaction products in a given time, the measurement becomes extraordinarily difficult because of the presence of high concentrations of reporter substrate molecules which have not been broken down.

SUMMARY

In accordance with the principles of the invention, artificially produced reporter substrate molecules with a very special structure together with corresponding preparation and measuring methods are used for the mass spectrometric measurement of the activities of selected endopeptidases. The reporter substrate molecules according to the invention each include a peptide with the cleavage motif of the endopeptidase whose cleavage activity is to be determined, an anchor group A1 on one side of the cleavage site and a different anchor group A2 on the other side of the cleavage site. The peptide with the cleavage motif is called a "cleavage peptide" here. The anchor groups are preferably attached to both ends of the cleavage peptide. The anchors A1 and A2 in the anchor groups are each protected against enzymatic digestion by protective groups and can be bound to the cleavage peptide by spacer groups in such a way that the cleavage is not sterically hindered. The anchor A1 serves to extract all undigested reporter substrate molecules in order to increase the dynamic range for the measurement of the cleavage products. The anchor group with the A2 anchor can contain a mass marker in addition to protective groups and spacer groups so that after cleavage and digestion of the remaining amino acids of the cleavage peptide by ever-present or added exopeptidases a stable anchor group with characteristic mass remains. This stable anchor group will be called an "indicator". The mass markers are specifically different for different types of cleavage peptide in the reporter substrate molecules to measure the activities of different endopeptidases in the same sample of body fluid. The indicators for the activities of the various endopeptidases selected appear side by side in the mass spectrum and can be quantitatively determined separately. The endopeptidases are unambiguously identified by the masses of the indicators.

In one embodiment, the invention provides a method with which the reporter substrate molecules are added in exact doses to a sample of the body fluid, for example a blood serum sample, the doses being chosen to be so high that the activity of the endopeptidases is not hindered by a lack of reporter substrate molecules. The sample of the body fluid is then incubated under carefully controlled conditions, the quantities of the reporter substrate molecules being cleaved then being proportional to the activity. After incubation, all reporter substrate molecules not enzymatically cleaved are removed by the first anchor A1, which also removes the cleavage products hanging on anchor A1. The second anchor A2 is then used to extract the reaction products hanging from this anchor from the body fluid. The quantities of these reaction products are determined mass spectrometrically. The prior removal of all uncleaved reporter substrate molecules serves to achieve a high dynamic range of measurement for the measurement of these reaction products extracted with anchor A2, since at low cleavage activity an enormous excess of uncleaved reporter substrate molecules remains. If they were to be left in the body fluid and also extracted with anchor A2, they would significantly interfere with the measurement of the reaction products on anchor A2 and greatly limit the dynamic range of measurement.

In another embodiment, after the undigested reporter substrate molecules have been extracted with anchor A1 one waits until the now terminally free-standing amino acids of the cleavage peptides on the reaction products on anchor A2 have been fully digested by the exopeptidases which are always present in the body fluid or have been additionally added so that, in each case, stable indicators remain which consist of anchor A2, protective groups, spacer groups and possibly mass markers. This reduction of the reaction products to the indicators simplifies the evaluation of the mass spectra, and the mass marker allows the method to be multiplexed by using several different reporter substrate molecules at the same time in the same sample.

The quantity of the reporter substrate molecules cleaved in a given time and hence the quantity of the reaction products produced, in the preferred case the quantity of the indicators produced, and in relation to the total amount of reporter substrate molecules used represents the activity of the endopeptidases in the body fluid. The quantitative mass spectrometric measurement of the indicators provides information relating to metabolic anomalies or diseases if they, as is the case for cancer, for example, are concomitant with the formation of characteristic endopeptidases or a change in their activities by the formation of coenzymes, for example.

In still another embodiment, in addition to the reporter substrate molecules, auxiliary substances can also be added which, like coenzymes, for example, affect the activity of the peptidases. Other auxiliary substances serve to allow the stable setting of a specified pH value. Exopeptidases can also be added in order to accelerate the digestion of the remaining amino acids of the cleavage peptide, i.e. the exposure of the indicators.

In particular, in yet another embodiment, precisely dosed quantities of stable reference substances can be added to the sample of the body fluid, said substances also carrying the anchor A2 and not being affected by enzymes in the sample. These reference substances can have the same structure as the indicators, with a mass marker which distinguishes them from the other indicators. These "reference indicators" are extracted from the sample with the indicator groups of the reporter substrate molecules and appear in the mass spectrum. They particularly serve as a quantitative reference in order to correct the combined influences on the measurements of destructive attacks on the indicators, variations in the extraction yield, and in particular of variations in the mass spectrometric sensitivity.

In another embodiment, the extraction of the reporter substrate molecules, their indicator groups and the reference substances with the aid of the anchors A1 and A2 can be carried out by immobilization on actively binding surfaces with subsequent washing; extraction and washing also bring the enzymatic activity to an end. The actively binding surfaces can be located on the inside surface of vessels or tubes or on the surface of microparticles or macroparticles; magnetic beads which are coated with immobilized capture substances are very easy to handle.

All types of mass spectrometer which are capable of ionizing and measuring organic substances with masses of several thousand atomic mass units can be used for the mass spectrometric measurements. Although very high mass resolution and mass accuracy are desirable here they are not absolutely necessary. Mass spectrometers with electrospray ion sources (ESI) or with ionization by matrix-assisted laser desorption (MALDI) are particularly suitable.

DETAILED DESCRIPTION

Figure 1:
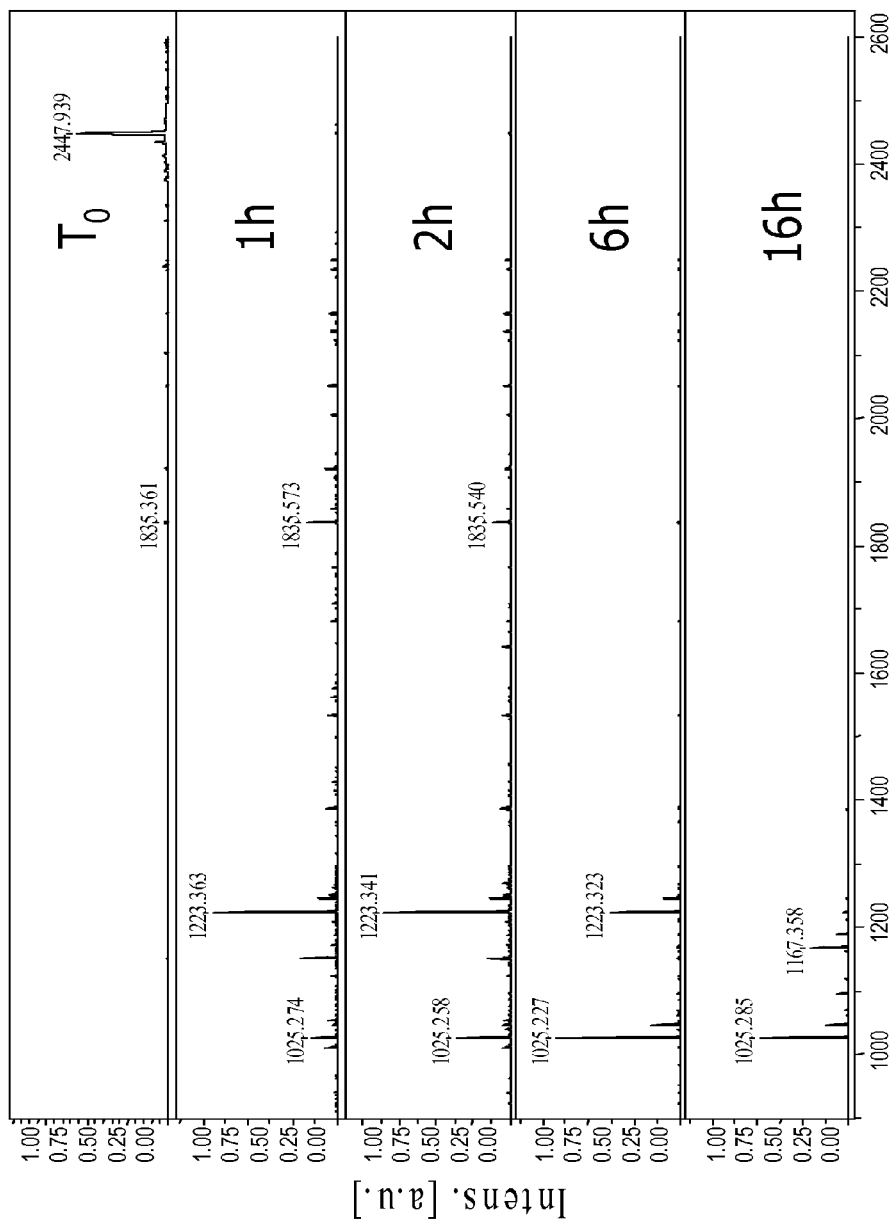
FIG. 1 shows the gradual digestion of a small quantity of the reporter substrate biotin-Abu-Ahx-ERGFFYTP-Ahx-HHHHHH-a (SEQ ID NO: 1) of mass m/z=2447 u in a sample of blood serum from tumor patients up to the pure indicator Ahx-HHHHHH-a (SEQ ID NO: 2) of mass m/z=1025 u (abbreviations are explained in the text). It can be seen here that the cleavage of this small quantity and the digestion to the specific fragment TP-Ahx-HHHHHH-a (SEQ ID NO: 3) of mass m/z=1225 u occur very rapidly, the further digestion without the addition of a corresponding exopeptidase is very slow, however. The signal at mass m/z=1835 is due to an artifact which has originated from the synthesis of the reporter substrate but which does not interfere here because of the rapid digestion. It should be noted here that this test run does not correspond to the diagnostic method, but is only intended to show the digestion of the amino acids of the cleavage peptide up to the indicator.

While the invention has been shown and described with reference to a number of embodiments thereof, it will be recognized by those skilled in the art that various changes in form and detail may be made herein without departing from the spirit and scope of the invention as defined by the appended claims.

The invention provides both the structural arrangement of special reporter substrate molecules which can be cleaved by the correspondingly selected endopeptidases, and also preparation and measurement methods for measuring the cleavage activity of the endopeptidases on these reporter substrate molecules.

The reporter substrate molecules according to the invention have a very special structure. They each contain a peptide with a cleavage motif for the endopeptidase whose cleavage activity is to be determined, and have anchor groups on both sides of the cleavage site, preferably at both ends of the peptide, said anchor groups containing one of two different types of anchor A1 and A2 for the extraction of the molecules from the body fluid. The anchor groups also contain protective groups against an enzymatic digestion of the anchors. Between the anchors and the cleavage peptides, spacer groups can facilitate the cleavage by the peptidases by removing steric hindrances. One of the anchors, anchor A1, for example, is intended to extract all undigested reporter substrate molecules. The other anchor group with the anchor A2 is then usually provided with mass markers in addition to protective and spacer groups which together form an "indicator" which is stable in the body fluid after the remaining amino acids of the cleavage peptide have been digested.

It is not absolutely necessary to digest the remaining amino acids of the cleavage peptide to the bare indicator because the reaction products can also be measured mass spectrometrically without this digestion. The digestion simplifies the mass spectrum, however, because the ladder of the digestion products is then limited to the indicator group. In combination with the mass markers of the indicators a multiplex method thus becomes possible which uses several different reporter substrate molecules in the same sample without the mass spectrometric signals overlapping.

The mass markers are specifically different for different types of cleavage peptide so that a common extraction of the different indicators and their mass spectrometric measurement allows the quantitative determination of the activities of the different endopeptidases selected from the same sample of body fluid in the same mass spectrum, the endopeptidases being identified by the masses of the assigned indicators.

A biotin which is bound to the amino terminus of the cleavage peptide via a protective group can serve as anchor A1, for example, allowing almost complete extraction of the attached substrate parts, and thus particularly all undigested reporter substrate molecules, by immobilized streptavidin. The protective group prevents the biotin being attacked by, for example, the biotinidase occurring in blood samples. 2-aminobutyric acid ("Abu") can be used as the protective group, for example. A spacer group can also be inserted between the Abu protective group and the cleavage peptide, 6-aminohexanoic acid ("Ahx", equivalent to aminocaproic acid "Acp"), for example, which is relatively long due to the hexane chain between amino group and acid group, and sterically simplifies the attack of the endopeptidase on the cleavage peptide. Both the protective groups and the spacer groups must be selected so they are not changed by enzymatic activity, and particularly that they cannot be removed by exopeptidases.

A 6-His tag can be used as the anchor A2, for example, which is bound to the carboxyl terminus via a spacer group and a protective group. The 6-His tag consists of six histidine amino acids and can easily be extracted by nickel ions which are bound to an immobilized chelate. Chelate-coated magnetic beads are commercially available. Here again, Ahx can also serve as the spacer group between the 6-His tag and the cleavage peptide and simultaneously as the protective group for the 6-His tag. The 6-His tag must carry a further protective group at the end in order to protect it from being digested by exopeptidases. Any amino acid which does not occur naturally and which cannot be changed enzymatically can serve here as the terminal protective group. A dextrorotatory amino acid, which does not interfere with the extraction, can favorably be used. For example, dextrorotatory alanine or threonine can be bound in this way. The various non-natural amino acids to protect the 6-His tags can also serve simultaneously as mass markers. In the following notation, dextrorotatory amino acids will be denoted by small letters, the conventional levorotatory amino acids will be denoted by capital letters. Instead of the non-natural amino acids on the 6-His tag it is also possible to stably introduce independent mass marker groups into the anchor group or to append them to the spacer group Ahx or to the 6-His tag. The use of dextrorotatory amino acids as both protective groups and mass markers makes it possible to construct around a dozen indicators of different mass including the reference indicators. This quantity can be further increased by other non-natural amino acids.

The endopeptidases whose activity is to be measured must of course be known. It is known from literature, for example, that colorectal cancer secretes the "cathepsin D" endopeptidase and the "cancer procoagulant" cystine protease into the blood during the formation of metastases or as more and more cells die. Cleavage motifs for these endopeptidases can be obtained from Internet databases, for example "Merops"; several cleavage motifs are usually known for these endopeptidases, sometimes around one hundred or more. The pattern ERGFFYTP (SEQ ID NO: 4), for example, can be used to measure the activity of cathepsin D, and the pattern WKPYDAAD (SEQ ID NO: 5) can be used for the cancer procoagulant. Both patterns are cleaved in the center. The pattern can also be extended if this seems appropriate.

A reporter substrate to measure the activity of cathepsin D can therefore look as follows: Biotin-Abu-Ahx-ERGFFYTP-Ahx-HHHHHH-a (SEQ ID NO: 1), where -a designates the dextrorotatory amino acid alanine, which serves as both protective group and mass marker. The indicator has the structure Ahx-HHHHHH-a (SEQ ID NO: 2) and a mass of 1025 atomic mass units. FIG. 1 shows a test run for the cleavage of a very small quantity of this reporter substrate in the blood serum of cancer patients and the digestion of the remaining amino acids of the cleavage peptide. It turns out that the cleavage is very rapid (in less than an hour), but the complete digestion of the free-standing amino acids of the cleavage peptide on the indicator occurs only very slowly without the addition of special exopeptidases. For a diagnostic method with indicators which are easy to measure it is also necessary to interpose a longer period of further incubation after the uncleaved reporter substrate molecules have been extracted or to support the usability of this reporter substrate by the addition of amino exopeptidases. The slow digestion of the last amino acids threonine-proline (TP) can be put down to the special structure of the proline, which is the only amino acid to have a ring structure between amino group and carboxylic acid. It is known from mass spectrometry that the electron-assisted fragmentation of multiply protonated peptides can also cleave all amino acids, but not the proline. It can therefore be better to use cleavage motifs without proline. Over one hundred cleavage motifs for cathepsin D are known from the Merops database.

The reporter substrate for cancer procoagulant can have the following structure, for example: Biotin-Abu-Ahx-WKPYDAAD-Ahx-HHHHHH-t (SEQ ID NO: 6), with dextrorotatory threonine -t as the protective group and simultaneously as the mass marker. This means the indicator now has the structure Ahx-HHHHHH-t (SEQ ID NO: 7, and with a mass of 1055 atomic mass units it differs from the above-mentioned indicator for cathepsin D by 30 mass units. Such large mass separations are not necessary, however; a mass difference of four atomic mass units is generally sufficient, which means that 11 of the 20 amino acids in their dextrorotatory form are suitable for this type of mass marker. Other amino acids which do not occur naturally can also be used, of course. After the reporter substrate has been cleaved, the digestion of the free-standing amino acids DAAD (SEQ ID NO: 8) on the indicator occurs very rapidly; here the few minutes between the extraction of the undigested reporter substrate by anchor A1 and the extraction of the indicators by anchor A2 already suffice to ensure that no intermediate digestion products can be seen in the mass spectrum. A pilot study has shown that this reporter substrate can successfully be used to diagnose colorectal cancer.

Figure 2:
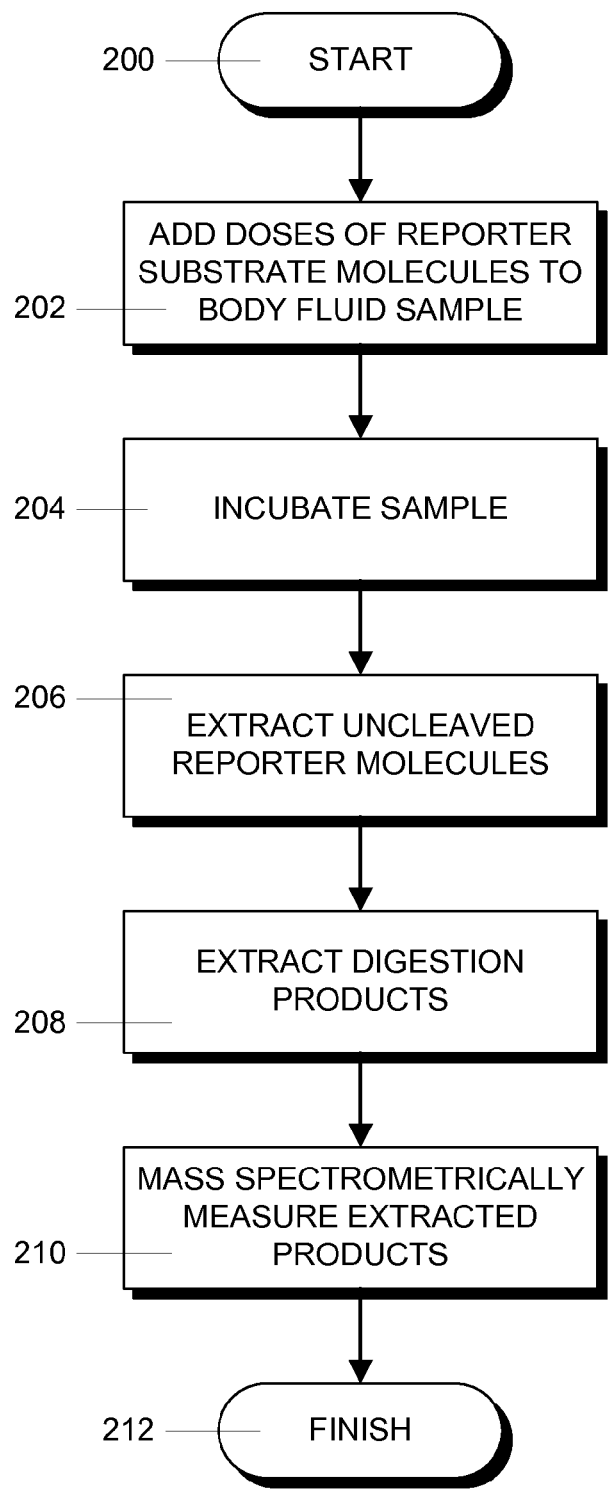
FIG. 2 is a flowchart showing the steps in an illustrative method for measuring the activity of endopeptidases in a body fluid.

The invention furthermore provides a method to measure the activity of endopeptidases as shown in FIG. 2. This method begins in step 200 and proceeds to step 202 where reporter substrate molecules for specific cleavages by the selected endopeptidases are added to a sample of body fluid, for example blood plasma or preferably blood serum, in exact doses. The doses are preferably so high that the activities of the endopeptidases selected are not slowed down by a lack of reporter substrate molecules. In step 204, the sample of the body fluid is then incubated under carefully controlled conditions, the quantity of reporter substrate cleaved then being proportional to the activity. Incubation time and incubation temperature are selected such that, at maximum activity, a maximum of ten percent of the reporter substrate molecules used are cleaved in order that differences in the activities of the endopeptidases in the body fluid can be measured for real and are not distorted by the lack of reporter substrate molecules. During the incubation period most of the free-standing amino acids of the cleavage peptides are already usually broken down by the exopeptidases which are always present in the body fluid or also additionally added, so that after the undigested reporter substrate molecules have been extracted it is very quickly the case that only stable indicators remain in each case, which consist of anchor A2, protective groups and mass markers.

Next, in step 206, after the incubation, all reporter substrate molecules which are not enzymatically cleaved are initially removed by the first anchor A1, a process which also removes the cleavage products hanging on anchor A1 so that they cannot be used to measure the activity. If test trials show that not all amino acids of the cleavage peptide are digested, it is preferable to include a further incubation period so that only bare indicators remain. In step 208, the indicators are extracted with the second anchor A2 from the sample, which is now liberated from the uncleaved reporter substrate molecules. The extraction method should be directed very specifically at substances with the anchor A2 in order to obtain mass spectra which are easy to interpret. Finally, in step 210, the quantities of the indicators extracted are determined mass spectrometrically. The prior removal of all uncleaved reporter substrate which would also be extracted with anchor A2 and interfere with the measurement of the indicators ensures that a significantly higher dynamic range of measurement is achieved for the measurement of the indicators extracted with anchor A2, compared to the situation where the uncleaved reporter substrate molecules are not removed. If one percent of dissolved reporter substrate is added to the body fluid, for example, the mass spectrometric measurement can preferably be designed for the range from 0.1 to 0.0001 percent of indicators. The method then finishes in step 212.

The quantity of the reporter substrate molecules cleaved in a given time and thus the quantity of the indicator groups generated represents the activity of the endopeptidases. The quantitative mass spectrometric measurement of the indicators provides information on the metabolic anomalies or diseases if, as is the case for cancer, for example, they are concomitant with the increased formation of characteristic endopeptidases or a change in their activities by the formation of coenzymes.

In addition to the reporter substrate molecules, auxiliary substances can also be added to the body fluid. Amino exopeptidases can be added, for example, in order to accelerate the digestion of the remaining amino acids of the cleavage peptide, i.e. the exposure of the indicators. Furthermore, auxiliary substances can be added which, like coenzymes, increase or stabilize the activity of the endopeptidases, or decelerate the activity of competing endopeptidases which attack the same cleavage motif. Further auxiliary substances can stabilize the pH value.

In particular, precisely dosed quantities of stable reference substances which also carry the anchor A2 and which are not changed by enzymes of the body fluid can be added to the sample of the body fluid. In a particularly preferred embodiment, these reference substances can have the same structure as the indicators, i.e. with an anchor A2, the same protective groups and spacer groups, and a mass marker which distinguishes it from the other indicators. The "reference indicators" are extracted from the sample with all other indicators of the digested reporter substrate molecules and appear in the mass spectrum. They serve as a reference for the quantitative determination of the indicators in the mass spectrum. The effect of destructive attacks on the anchor A2, variations in the extraction yield, and in particular fluctuations in the mass spectrometric sensitivity on the measurements can thus be corrected together.

The reference indicators can also serve as a mass reference, however. For an accurate mass determination many mass spectrometric measurements require a so-called "internal mass reference", which supplies a signal in the mass spectrum against which the other mass signals can be referenced. In FIG. 1 it is clearly to be seen how the given masses of the same mass signals vary slightly, because they have been computed without the use of such an internal mass reference.

The extraction of the reporter substrate molecules, their indicator groups and the reference substances with the aid of the anchors A1 and A2 can preferably be carried out by immobilization on actively binding surfaces with subsequent washing; extraction and washing also bring the enzymatic activity to an end. The coatings with capture substances which are used for the extractions can be located on the interior surfaces of vessels, on filter material with various types of structure—felts, nonwovens or open-pored solid foams—or on the surfaces of macroscopic or microscopic packing pellets. Microscopic packing pellets can be present in the form of stable suspensions. These packing pellets can be separated by filtration or by centrifugation. Macroscopic packing pellets in form of small magnetic beads as mentioned above are particularly suitable since they can be moved through the liquid with magnets. They can be held on the walls of the vessel by magnetic forces, for example, in order to exchange blood serum or other body fluids for washing liquid after the indicators have been immobilized. Automatic pipetting devices which contain devices for treating liquids with magnetic beads are commercially available.

The bead accumulations adhering to the wall or sedimented are then freed from the sample solution by draining or pipetting, and a washing liquid is added. The beads are washed by removing the magnet and stirring. The stirring can also be brought about by magnetic forces. The washing process can be repeated several times when necessary. Finally an eluting fluid, which separates the indicators from the capture molecules on the magnetic beads, is added to the accumulation of beads which should be almost free from any liquid. Such eluting fluids are often strong, polar organic solvents such as acetone, acetonitrile or alcohols, but can also be acidic media. The eluting fluids with the indicators are then transferred to the mass spectrometric measurement.

Biotin groups of the reporter substances, for example, can thus be bound to immobilized streptavidin in the familiar way. Biotin is a non-protein substance (molecular weight 244.3 atomic mass units). The specialist is familiar with the method of bonding biotin to proteins. Streptavidin is a protein with a molecular weight of 50 to 60 kilodaltons which very specifically bonds the biotin and the digest products which are covalently bound with it. Streptavidin can be covalently bound to solid surfaces, as the specialist is also aware. Microtitration plates with streptavidin coatings on the inside surfaces of the microvessels and suspensions with coated microparticles ("slurry") are commercially available, for example. Also commercially available are magnetic beads which are prepared for the bonding of streptavidin.

It is also possible to use other chemical groups as the anchors instead of the biotin. If these anchors do not bind reversibly to the immobilized capture substances used, the anchor groups can also be bound to the reporter substrate molecules via cleavable linkers. Many types of such linkers are known. Particularly convenient are photolytically cleavable linkers which can be irreversibly cleaved without the addition of chemicals under a UV lamp. It is also possible to use chemically, thermally or enzymically cleavable linkers.

The previously mentioned 6-His tags of the anchor group 2 can be reversibly captured by nickel, which is bound to immobilized chelates. Magnetic beads which are prepared in such a way that they can easily be coated with nickel ions from nickel salts are also commercially available for this purpose.

Methods according to this invention can be used for a wide variety of analyses. It is thus possible to study the catalytic operation of enzymes in blood in a general way under different conditions on different reporter substrate molecules in medical research, or to investigate the effectiveness of pharmacologically active substances in pharmacological Research and Development. It is possible to optimize the dosing of drugs if they are used for diseases or metabolic anomalies which are linked to changed activities of enzymes which act in a specific way. The effect of many drugs is based on a change in the activity of enzymes, they can act as activators or inhibitors. The methods can also be used to search for or develop favorable reporter substrate molecules, however.

To develop diagnostic methods, the types of the reporter substrate molecules, the quantities to be added and the incubation conditions in particular must be optimized. Varying the reporter substrate molecules allows those reporter substrate molecules to be identified which result in significant differences in the quantity of the indicators formed in the body fluids of different cohorts of healthy and ill patients.

To evaluate the mass spectra with several indicators in samples of cohorts of precisely characterized patients, computer programs are commercially available which generally use statistical methods to work out significantly different indicator patterns. By applying these programs to mass spectra which have been obtained by adding different types of reporter substances using different method parameters, the method can be optimized to determine disease-specific enzyme activities in the usual way.

If such a method of determining disease-specific enzyme activities is developed and optimized with the aid of the indicator patterns, the method with the optimum reporter substances and the optimum method parameters can be used to measure the enzyme activities. Comparative measurements of the enzyme activities are used in many fields of medical and biological research. If these measurements are intended to be used for diagnostic purposes, and if these diagnostic measurements are to be applied across the board in several laboratories, the method must be validated in Europe according to the IVD Directives, as was mentioned in the introduction. In the USA it must be validated by the FDA (Food and Drug Administration).

For diagnostic methods for the detection of certain diseases or metabolic anomalies, it is particularly possible to develop disease-specific analyses kits which contain all substances to be added to the body fluid together in pre-prepared portions. Each of these kits can contain several reporter substrate molecules, one or more suitable reference indicators, exopeptidases to digestion the remaining amino acids of the respective cleavage peptide, and other auxiliary substances. Moreover, the analyses kits can contain the agents for the extraction by reversible bonding to suitable capture substances where the capture substances are preferably immobilized on solid surfaces. For example, the analyses kits can contain magnetic beads with capture substances for both anchors A1 and A2; they can also contain fluids for releasing the indicators from the capture substances.

Mass spectrometers with ionization by matrix-assisted laser desorption (MALDI) as well as by electrospray ionization (ESI) can be used for the quantitative analysis of the indicators. Different types of time-of-flight mass spectrometer and also ion cyclotron resonance or ion trap mass spectrometers can be used.

In the case of MALDI time-of-flight mass spectrometers the solution of the indicators released from the capture substances is dried in on a sample support after a suitable matrix has been added. Particularly suitable are commercially available sample supports, which are already coated with a thin layer of the matrix substance; these particularly provide good quantitative behavior. The solid sample on the sample support is then bombarded with flashes of laser light in the ion source of the mass spectrometer; the ions created are separated by their time of flight in the time-of-flight mass spectrometer according to their mass, detected in an ion detector and measured according to their quantity. This process of ionization using matrix-assisted laser desorption (MALDI) provides predominantly only singly charged intact ions of the molecules; the mass spectrum is thus a true representation of the profile of the extracted reaction products, as can be seen from FIG. 1.

The solution with the indicators can either be introduced directly to a mass spectrometer with electrospray ion source (ESI) or introduced to the mass spectrometer after having been separated again by a chromatograph. This type of ionization also supplies multiply charged ions of the analyte molecules, however; the mass spectrum is therefore more difficult to evaluate, but offers good quantitative evaluation possibilities. Time-of-flight mass spectrometers with orthogonal injection of the ions can be used as the mass spectrometer, as can ion trap mass spectrometers.

With knowledge of this invention, those skilled in this art can develop further embodiments of the reporter substrate molecules and methods.

What is claimed is:

1. A method for determining activity of at least one endopeptidase in a body fluid comprising:
   (a) adding to the body fluid a dose of at least one reporter substrate, the molecules of which include a peptide having a cleavage motif of the at least one endopeptidase and that has a cleavage site with a first anchor located on one side of the cleavage site and a second anchor that differs from the first anchor located on another side of the cleavage site;
   (b) incubating the fluid resulting from step (a) for a predetermined time under predetermined conditions, so that added reporter substrate molecules are subjected to enzymatic activity of endopeptidases and exopeptidases contained in the body fluid;
   (c) extracting all molecules carrying one of the two anchors so that all reporter substrate molecules not cleaved are extracted;
   (d) extracting any remaining reaction products using the anchor not used in step (c); and
   (e) measuring the reaction products extracted in step (d) by mass spectrometry to determine the quantity thereof, which in relation to an amount of reporter substrate molecules in the dose used in step (a) represents activity of the at least one endopeptidase.

2. The method of claim 1, wherein between steps (c) and (d) a further incubation of the fluid is carried out for a predetermined time under predetermined conditions.

3. The method of claim 1, wherein exopeptidases are added to the body fluid in step (b) so that the added exopeptidases digest the exposed amino acids of the cleavage peptide after a cleavage.

4. The method of claim 1, wherein one or more reference substances are added to the fluid for quantitative determinations before step (d), each reference substance containing the anchor used in step (d) and thus also being extracted in step (d).

5. The method of claim 1, wherein auxiliary substances are added to the body fluid in step (a), the auxiliary substances forming co-enzymes with enzymes present in the body fluid in order to stabilize and assist enzymatic activity.

6. The method of claim 1, wherein the determination of the endopeptidases activity is used for medical diagnoses of diseases.

7. The method of claim 1, wherein the determination of the endopeptidases activity is used to analyze metabolic anomalies.

8. The method of any one of claims 1 to 5, wherein the determination of the endopeptidase activity is used to analyze effectiveness of pharmacologically active substances.

9. The method of claim 1 wherein, in step (a), the dose comprises a plurality of reporter substrates, each reporter substrate corresponding to a specific endopeptidase, including a peptide having a cleavage motif of each specific endopeptidase and having a cleavage site with the first anchor located on one side of the cleavage site and the second anchor located on another side of the cleavage site.

* * * * *